US008688216B2

(12) United States Patent
Yost et al.

(10) Patent No.: US 8,688,216 B2
(45) Date of Patent: Apr. 1, 2014

(54) AUTOTHRESHOLD WITH SENSING FROM PACING CATHODE

(71) Applicant: Cardiac Pacemakers, Inc., St. Paul, MN (US)

(72) Inventors: David W. Yost, Brooklyn Park, MN (US); Deepa Mahajan, Circle Pines, MN (US); Clayton S. Foster, Andover, MN (US); Aaron R. McCabe, Edina, MN (US); Shibaji Shome, Arden Hills, MN (US); Amy Jean Brisben, Saint Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/684,814

(22) Filed: Nov. 26, 2012

(65) Prior Publication Data
US 2013/0138174 A1    May 30, 2013

Related U.S. Application Data

(60) Provisional application No. 61/564,676, filed on Nov. 29, 2011.

(51) Int. Cl.
*A61N 1/00*          (2006.01)
(52) U.S. Cl.
USPC .......................................................... 607/28
(58) Field of Classification Search
USPC .................. 607/28, 9, 18, 25, 27, 62, 122
See application file for complete search history.

(56) References Cited

U.S. PATENT DOCUMENTS

| | | |
|---|---|---|
| 4,979,507 A | 12/1990 | Heinz |
| 5,683,431 A | 11/1997 | Wang |
| 6,016,446 A | 1/2000 | Belalcazar |
| 6,044,296 A | 3/2000 | Zhu et al. |
| 6,061,594 A | 5/2000 | Zhu et al. |
| 6,128,535 A | 10/2000 | Maarse |
| 6,226,551 B1 | 5/2001 | Zhu et al. |
| 6,298,269 B1 | 10/2001 | Sweeney |
| 6,311,089 B1 | 10/2001 | Mann et al. |
| 6,324,427 B1 | 11/2001 | Florio |
| 6,327,498 B1 | 12/2001 | Kroll |
| 6,427,085 B1 | 7/2002 | Boon et al. |
| 6,430,441 B1 | 8/2002 | Levine |
| 6,505,071 B1 | 1/2003 | Zhu et al. |
| 6,539,262 B2 | 3/2003 | Sweeney |
| 6,618,621 B1 | 9/2003 | Holmstrom |
| 6,714,819 B1 | 3/2004 | Sloman |
| 6,731,985 B2 | 5/2004 | Poore et al. |
| 6,738,668 B1 | 5/2004 | Mouchawar et al. |

(Continued)

*Primary Examiner* — Robert N Wieland
(74) *Attorney, Agent, or Firm* — Schwegman, Lundberg & Woessner, P.A.

(57) ABSTRACT

Cardiac electrostimulation energy is delivered to a heart chamber of a subject according to a normal pacing mode using a set of implantable pacing electrodes. When a threshold test for the heart chamber is initiated and a sensing electrode independent from the set of pacing electrodes is unavailable for the heart chamber, cardiac electrostimulation energy is delivered to the subject according to a threshold test mode. The threshold test mode includes sensing a cardiac activity signal from a subject using a set of sensing electrodes that includes an electrode common to the set of pacing electrodes, and changing the electrostimulation energy and sensing a resulting cardiac activity signal using the set of sensing electrodes to determine the optimum electrostimulation energy for capture of the heart chamber.

20 Claims, 5 Drawing Sheets

(56) References Cited

U.S. PATENT DOCUMENTS

| | | |
|---|---|---|
| 6,757,563 B2 | 6/2004 | Sweeney |
| 6,928,326 B1 | 8/2005 | Levine |
| 6,973,350 B1 | 12/2005 | Levine et al. |
| 7,031,773 B1 | 4/2006 | Levine et al. |
| 7,099,716 B1 | 8/2006 | Levine |
| 7,158,831 B2 | 1/2007 | Zhu |
| 7,177,689 B2 | 2/2007 | Ternes et al. |
| 7,181,280 B1 | 2/2007 | Sloman |
| 7,286,874 B1 | 10/2007 | Bornzin |
| 7,308,310 B1 | 12/2007 | Levine et al. |
| 7,424,323 B1 | 9/2008 | Reiss et al. |
| 2008/0071319 A1 | 3/2008 | Sathaye et al. |
| 2009/0149905 A1 | 6/2009 | Lyden et al. |
| 2011/0098773 A1 | 4/2011 | Brisben et al. |
| 2011/0245890 A1 | 10/2011 | Brisben et al. |
| 2012/0130442 A1* | 5/2012 | Rockweiler et al. ............ 607/18 |

* cited by examiner

AUTOTHRESHOLD WITH SENSING FROM PACING CATHODE

CLAIM OF PRIORITY

This application claims the benefit of priority under 35 U.S.C. §119(e) of Yost et al., U.S. Provisional Patent Application Ser. No. 61/564,676, filed on Nov. 29, 2011, the benefit of priority of which is claimed hereby, and is incorporated by reference herein in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. In response to an abnormally slow heart rate some CFM devices deliver electrical pacing stimulation energy to induce cardiac depolarization and contraction (sometimes called capture of the heart). The stimulation energy is delivered to provide a depolarization rate that improves hemodynamic function of the patient. It is desirable to optimize the pacing stimulation energy delivered when pacing the heart to ensure therapy delivery and yet avoid stressing the heart unnecessarily and compromising battery life.

Overview

This document relates generally to systems, devices, and methods that provide electrical pacing therapy to the heart of a patient or subject. In particular it relates to, systems, devices, and methods to automatically determine a pacing capture threshold of the heart of a patient or subject.

An apparatus example includes a therapy circuit, a cardiac signal sensing circuit, and a control circuit communicatively coupled to the cardiac signal sensing circuit and the therapy circuit. The therapy circuit provides cardiac electrostimulation energy to a heart chamber of a subject using a set of implantable pacing electrodes and the cardiac signal sensing circuit senses a cardiac activity signal. The control circuit initiates delivery of electrostimulation energy to the heart chamber according to a normal pacing mode, and initiates a first threshold test mode when receiving an indication to start a threshold test for the heart chamber and a sensing electrode independent from the set of pacing electrodes is unavailable for the heart chamber. When in the first threshold test mode, the control circuit recurrently changes the electrostimulation energy delivered to the heart chamber, receives a cardiac activity signal sensed using a set of sensing electrodes that includes an electrode common to the set of pacing electrodes, and determines an optimum electrostimulation energy for capture of the heart chamber using the sensed cardiac activity signal.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

As explained above, pacing stimulation energy should be optimized for a patient. If the pacing energy is too high, the stimulation may cause stress on the heart and the battery life of an implanted device will be needlessly short. If the pacing stimulation energy is too low, the pacing energy will not evoke a response in the heart (i.e., will not induce capture of the heart, which is a cardiac depolarization that results in contraction). Tests can be run by IMDs to determine an optimum energy threshold for pacing therapy. The optimum threshold is the minimum level of stimulus energy that will induce capture in excitable cardiac tissue. In other words, the tests automatically try to find the minimum electrical stimulation required to consistently cause a cardiac depolarization. The optimum threshold may vary over time for a patient due to maturation of myocardial tissue around an implanted electrode, drug therapy prescribed to the patient, an episode of myocardial infarction, and defibrillation of the myocardial tissue. Therefore, the tests are run more than once by a device while the device is implanted.

Figure 1:
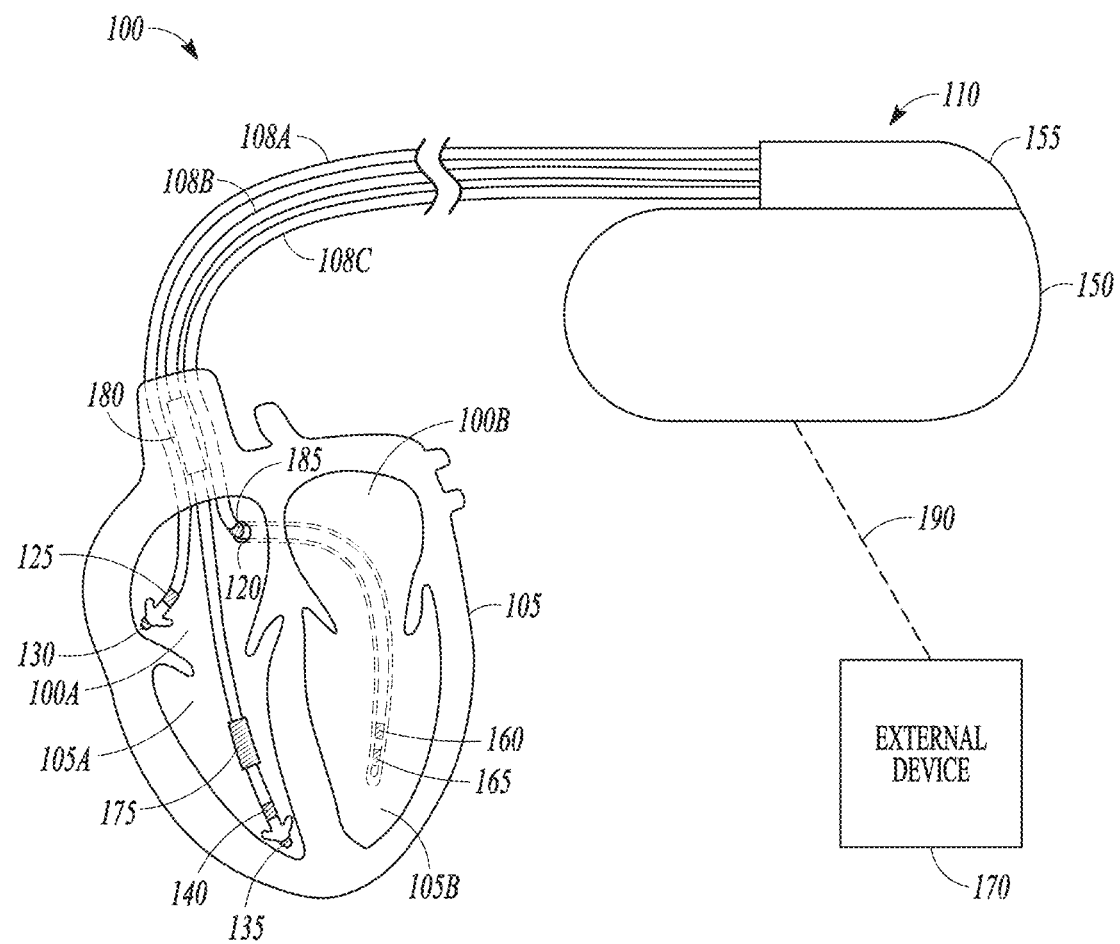
FIG. 1 is an illustration of portions of an example of a system that uses an IMD.

FIG. 1 is an illustration of portions of a system that uses an IMD 110. Examples of IMD 110 include, without limitation, a pacer, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals. The external device 170 may communicate with a remote system via a network, such as a computer network or cellular phone network. In some examples, the remote system provides patient management functions and may include one or more servers to perform the functions.

The IMD 110 is shown coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes can be electrically coupled to sense amplifiers to sense electrical cardiac signals. Sometimes the sensing circuits and electrodes are referred to as channels. For example, circuitry used to sense signals in an atrium is referred to as an atrial sensing channel, and circuitry used to sense signals in a ventricle is referred to as a ventricular sensing channel. When direction is taken into account due to position of one or more sensing electrodes, the sensing channel can be referred to as a sensing vector.

Sensed electrical cardiac signals can be sampled to create an electrogram (sometimes called an egram). An electrogram can be analyzed by the IMD 110 and/or can be stored in the IMD 110 and later communicated to the external device 170 where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 120.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, the present methods and systems apply to a variety of configurations and with a variety of electrodes. Other forms of electrodes include meshes and patches which may be applied to portions of heart 105 or which may be implanted in other areas of the body to help "steer" electrical currents produced by IMD 110. An IMD may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Figure 2:
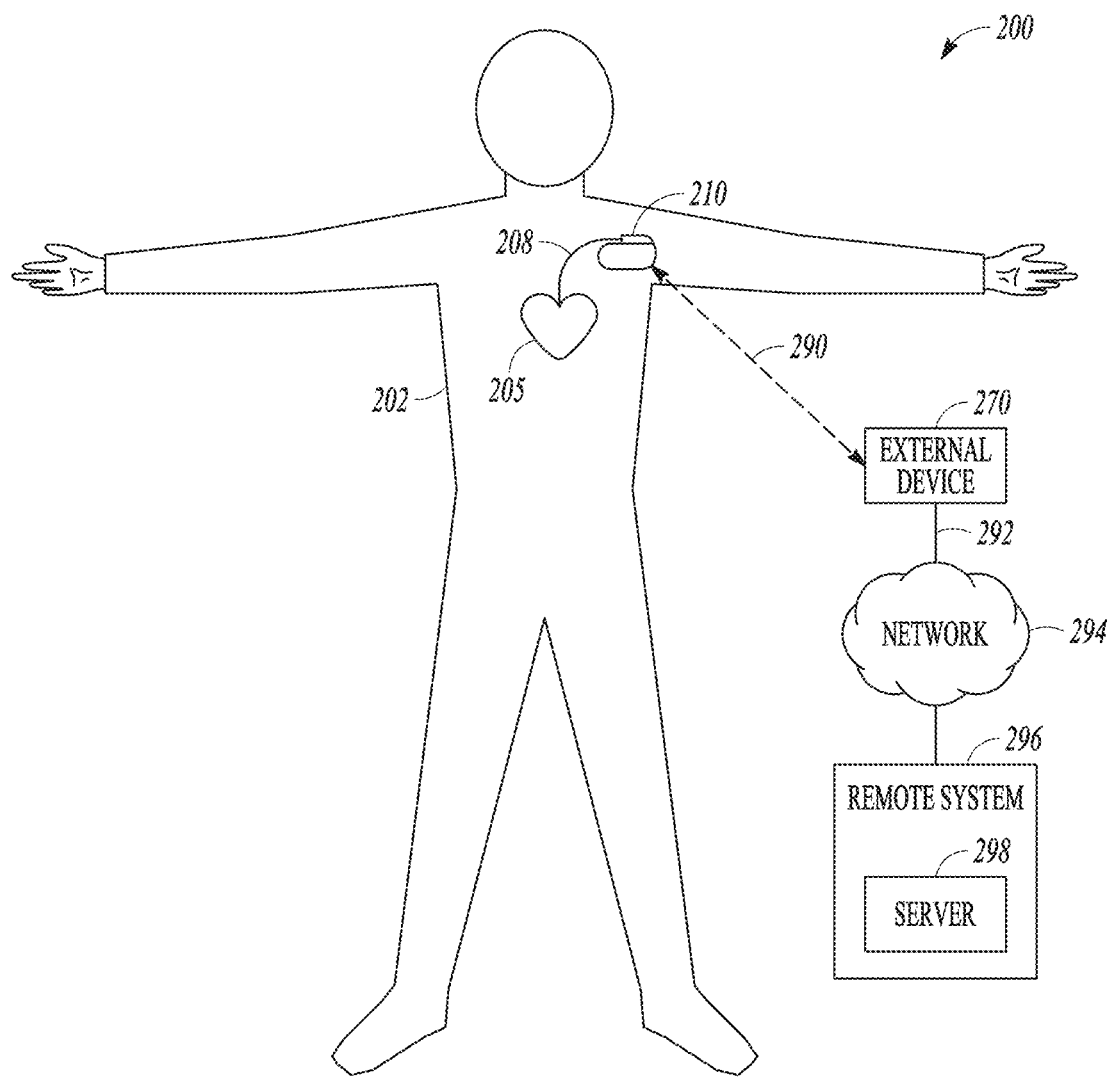
FIG. 2 is an illustration of portions of another example of a system that uses an IMD.

FIG. 2 is an illustration of portions of another system 200 that uses an IMD 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicated via the network using a link 292 that may be wired or wireless. In some examples, the remote system 296 provides patient management functions and may include one or more servers 298 to perform the functions.

Medical device based tests can be performed to automatically determine an optimum pacing threshold for the patient. This pacing threshold is ideally the minimum electrostimulation energy required to evoke a response or induce capture of a chamber of the heart. To determine appropriate pacing electrostimulation energy, the device delivers a sequence of electrostimulation pulses to the heart. The sequence may include a successive reduction of the energy of the electrostimulation pulses. A first electrostimulation pulse that will likely induce capture is delivered. The energy of subsequent electrostimulation pulses is reduced in steps until the device verifies that failure to induce capture has occurred. Alternatively, the sequence may include increasing the energy of the electrostimulation pulses. A first electrostimulation pulse that is below a threshold likely to induce capture is delivered. The energy of subsequent electrostimulation pulses is increased in steps until the device verifies that capture was induced.

The device uses information obtained from the threshold test or autothreshold test to recommend a pacing output setting, automatically adjust a pacing output setting, or merely store a pacing output setting for later access. The threshold test can be executed when a prompt is received by the device to begin a test or the device can be programmed to recurrently run the test according to a programmed schedule (e.g., daily, weekly, etc.). An approach for an automatic capture threshold test (or autothreshold test) can be found in U.S. Patent Pub. No. US 2008/0071319, by Sathaye et al., filed Sep. 14, 2006, and entitled "Capture Detection with Cross Chamber Backup Pacing," which is incorporated herein by reference in its entirety.

The threshold test can be run for any heart chamber. Typically, two or more electrodes are used to provide the electrostimulation pulse, and two or more electrodes separate from the pacing electrodes are used to sense the resulting depolarization to detect capture of the heart chamber. For the example of FIG. 1, there are six pacing vectors available for the LV: i) LV Tip electrode to Can electrode (LVTip-Can), ii) LV Ring electrode to Can electrode (LVRing-Can), iii) LV Tip electrode to Right Ventricular electrode (LVTip-RV), iv) LV Ring electrode to Right Ventricular electrode (LVRing-RV), v) LVTip-LVRing, and vi) LVRing-LVTip.

The first four of the six listed pacing vectors include a sensing vector option for the LV. For example, if the pacing vector is LVTip-Can, LVRing-Can is available as a sensing vector. In another example, if the pacing vector is LVRing-RV, LVTip-RV is available as a sensing vector. Note however, for vectors (v) and (vi) that a sensing electrode independent of the pacing vector is not available. In these two cases, the electrodes of the bipolar lead at the LV are both dedicated to bipolar pacing, and a sensing electrode is unavailable for the LV chamber. It can be seen that the same would be true if the LV lead was a unipolar lead and unipolar pacing was used in the LV. No independent sensing electrode is available to detect and verify capture of the LV for a unipolar LV lead configuration. Thus, there is a need for a different approach to executing a threshold test when an independent sensing electrode is unavailable.

Figure 3:
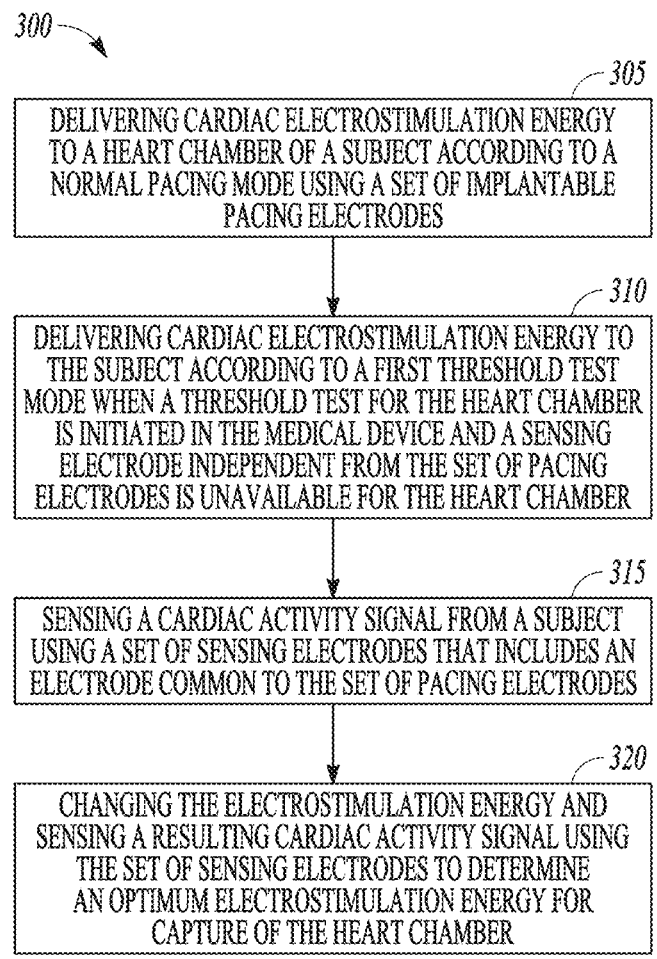
FIG. 3 is a flow diagram of an example of a method of operating a medical device to perform a capture threshold test.

FIG. 3 is a flow diagram of an example of a method 300 of operating a medical device to perform an automatic capture threshold test. At block 305, cardiac electrostimulation energy is delivered to a heart chamber of a subject according to a normal pacing mode using a set of implantable pacing electrodes. The normal pacing mode can be used to treat bradycardia and the heart chamber can be any of the left atrium (LA), RA, RV, or LV.

At block 310, cardiac electrostimulation energy is delivered to the subject according to a first threshold test mode when a threshold test for the heart chamber is initiated in the medical device and a sensing electrode independent from the set of pacing electrodes is unavailable for the heart chamber. As explained herein, a sensing electrode independent from the pacing channel can be unavailable for the heart chamber if the electrode configuration includes a lead for the heart chamber that comprises a bipolar electrode pair and the electrode pair is dedicated to pacing, or the electrode configuration includes a unipolar lead for the chamber which is dedicated to pacing.

The first threshold test mode includes, at block 315, sensing a cardiac activity signal from a subject using a set of sensing electrodes that includes an electrode common to the set of pacing electrodes. For example, if a bipolar electrode pair is dedicated for pacing the LV, one of the electrodes (LVTip or LVRing) can be included in a set of sensing electrodes that includes a RV electrode or the can electrode. At block 320, the first threshold test mode includes changing the electrostimulation energy and sensing a resulting cardiac activity signal using the set of sensing electrodes to determine the optimum electrostimulation energy for capture of the heart chamber.

For example, the normal pacing mode can include delivering electrostimulation pulses to the LV using the LVTip and LVRing, and the first threshold test mode can include determining the optimum electrostimulation energy for capture of the LV using the LV Tip or LVRing.

Figure 4A:
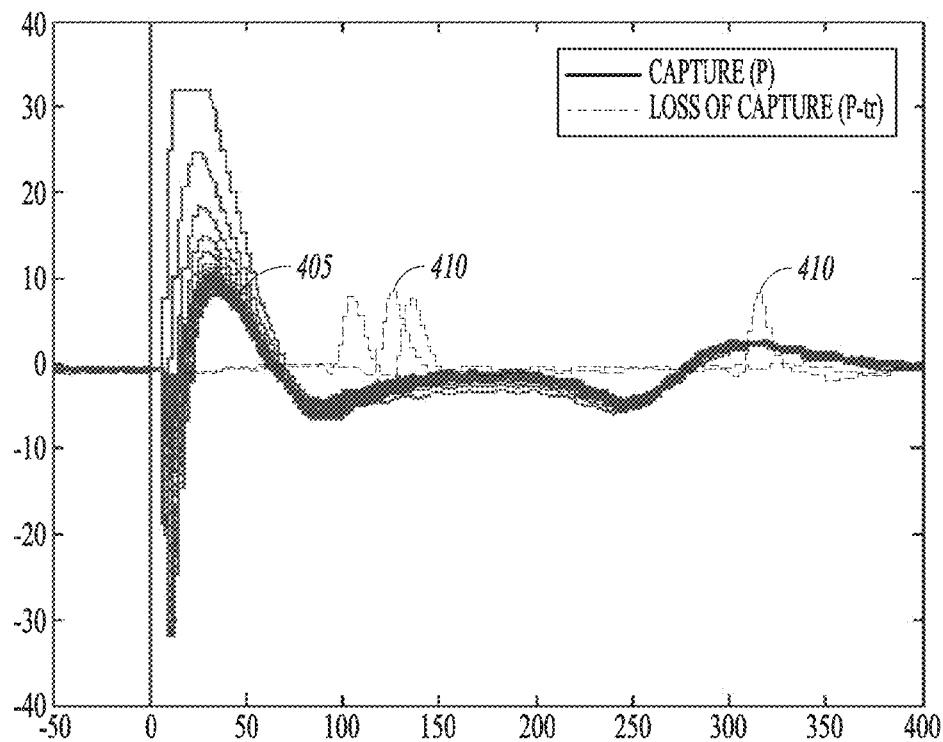
FIGS. 4A and 4B show graphs of examples of performing a threshold test for the left ventricle.

FIG. 4A shows a graph of an example performing a threshold test for the LV when a sensing electrode independent from the set of pacing electrodes is unavailable for the heart chamber. The electrode configuration for the LV includes a lead having a bipolar electrode pair, and the bipolar electrode pair is dedicated to pacing the LV. To sense cardiac depolarizations to perform the threshold test, the cathode is shared between the set of pacing electrodes and the set of sensing electrodes (LVTip to Can) used in the test. The threshold test starts with a pacing voltage of 7.5 Volts (V) and decreases the pacing amplitude over fifteen test steps. Loss of capture of the LV occurs when the amplitude decreases to 1.3 V and can be detected based on the timing of the peaks of the depolarization. Based on the results of the test, the pacing amplitude can be set to the amplitude of the step immediately previous to the 1.3V step, or an amplitude safety margin can be added to the 1.3V step or to the amplitude of the step immediately previous to the 1.3V step. The graph shows the distinction between capture 405 and loss of capture 410. Note that the there is an initial peak variation for capture over the 5-7 beats that start the test. This can be addressed by adding a stabilization phase to the beginning of the threshold test before decreasing the pacing amplitude.

Figure 4B:
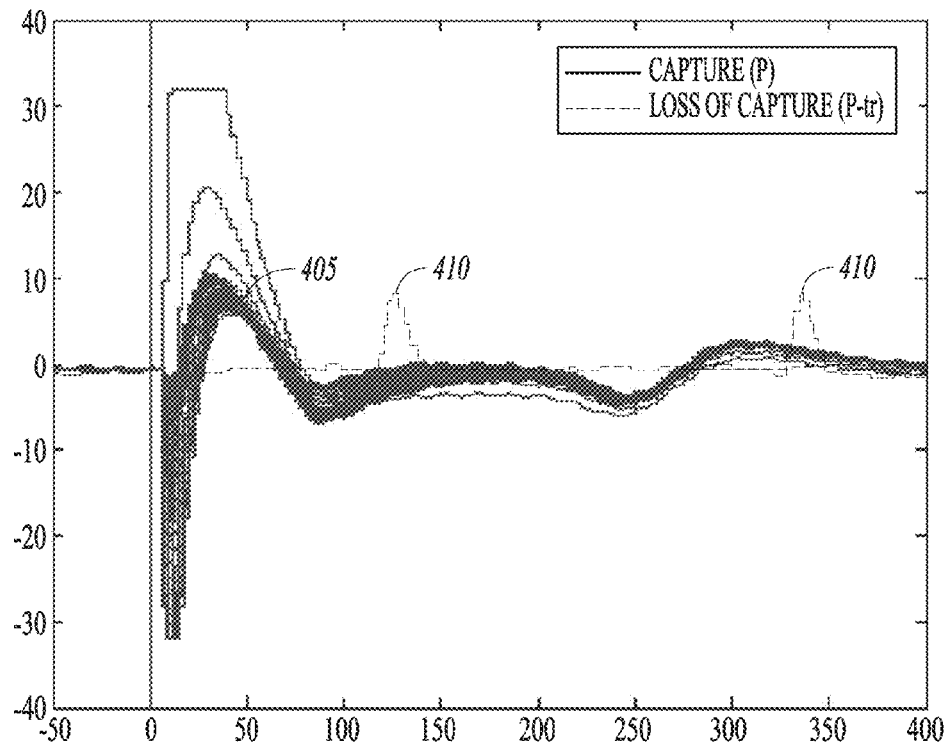

FIG. 4B shows a graph of another example performing a threshold test for the LV when a sensing electrode independent from the set of pacing electrodes is unavailable for the heart chamber. The electrode configuration for the LV includes a lead configured for unipolar pacing of the LV (e.g., LVTip to RV). To sense cardiac depolarizations to perform the threshold test, the cathode is again shared between the set of pacing electrodes and the set of sensing electrodes (LVTip to Can) used in the test. The threshold test again starts with a pacing voltage of 7.5 Volts (V) and decreases the pacing amplitude over fifteen test steps. Loss of capture of the LV in this test example occurs when the amplitude decreases to 0.8 V. The distinction between capture 405 and loss of capture 410 is again evident in the graph.

Figure 5:
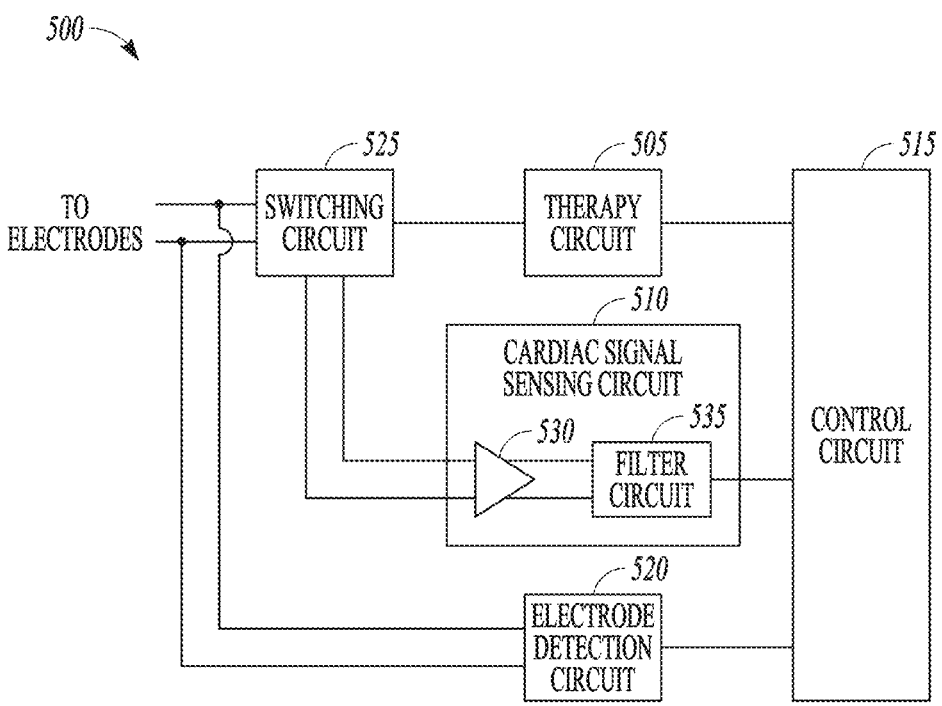
FIG. 5 shows a block diagram of portions of an example of a medical device for performing a pacing threshold test.

FIG. 5 shows a block diagram of portions of an example of a medical device for performing a pacing threshold test. The device 500 includes a therapy circuit 505, a cardiac signal sensing circuit 510, and a control circuit 515. The therapy circuit 505 provides cardiac electrostimulation energy to a heart chamber of a subject using a set of implantable pacing electrodes, and the cardiac signal sensing circuit 510 senses a cardiac activity signal using a set of sensing electrodes.

The control circuit 515 can be a processor, a digital signal processor (DSP), application specific integrated circuit (ASIC), microprocessor, or other type of processor, interpreting or executing instructions in software modules or firmware modules. The control circuit 515 can include other circuits or sub-circuits to perform the functions described. These circuits may include software, hardware, firmware or any combination thereof. Multiple functions can be performed in one or more of the circuits as desired. The control circuit 515 is communicatively coupled to the therapy circuit 505 and the cardiac signal sensing circuit 510. The communicative coupling allows signals to be communicated among the control circuit 515, the therapy circuit 505, and the cardiac signal sensing circuit 510 even though there may intervening circuitry between the control circuit 515, the therapy circuit 505, and the cardiac signal sensing circuit 510.

The control circuit 515 initiates delivery of electrostimulation energy to the heart chamber according to a normal pacing mode, such as to treat bradycardia of the subject for example. The control circuit 515 initiates a first threshold test mode when receiving an indication to start a threshold test for the heart chamber and a sensing electrode independent from the set of pacing electrodes is unavailable for the heart chamber. The indication to begin a threshold test may be a prompt or command to execute the test communicated from a second separate device, or the indication may originate within the device 500, such as by being programmed to recurrently run a threshold test.

To determine whether a sensing electrode is available or unavailable for the heart chamber, the device 500 may include a memory circuit integral to, or communicatively coupled to, the control circuit 515. An electrode configuration for a system that includes the device can be stored into the memory circuit at the time of implant. The control circuit 515 can determine the electrode configuration and whether a sense electrode is available by reading the stored electrode configuration.

In some examples, the device 500 includes an electrode detection circuit 520 communicatively coupled to the control circuit 515. In certain examples, the electrode detection circuit 520 can determine an electrode configuration by measuring impedance at device connectors, such as lead connectors included in a header of the device. A very large measured impedance value would indicate that an electrode or lead is not present and a lower impedance value would indicate that an electrode or lead is present.

When in the first threshold test mode, the control circuit 515 recurrently changes the electrostimulation energy delivered to the heart chamber using the set of pacing electrodes of the pacing vector. The control circuit 515 receives a cardiac activity signal sensed using a set of sensing electrodes that includes an electrode common to the set of pacing electrodes, and determines an optimum electrostimulation energy for capture of the heart chamber using the sensed cardiac activity signal.

Executing a threshold a test when there is an electrode common to both the pacing vector and the sensing victor may make it difficult to sense the cardiac depolarization resulting from electrostimulation of the test. Typically, a blanking period is initiated in the electronic sensing circuits. These cardiac signal sensing circuits are used to detect an intrinsic cardiac depolarization. In some examples, sense amplifiers included in the cardiac signal sensing circuits are blanked by being electrically disconnected or otherwise electrically isolated from the sensing electrodes. After a specified period of time the sense amplifiers are electrically reconnected to the electrodes. The blanking period prevents the sense amplifiers from being swamped by the electrostimulation energy from the pace pulse.

When a threshold test is desired and there is an independent sensing electrode available, there is no timing issue and the threshold test can be run with the pacing blanking period. However, as shown in the examples of capture in FIGS. 4A, 4B, using a blanking period when a sensing electrode is not available may mask the capture of heart chamber. Changing the blanking period can resolve this signal sensing issue.

The blanking period can include a recharge time duration. The set of pacing electrodes are electrically coupled together during recharge. This helps dissipate any residual charge at the electrode-tissue interface after an electrostimulation pulse is delivered. In some examples, the device 500 includes a switching circuit 525 communicatively coupled to the set of sensing electrodes, the set of pacing electrodes, and the control circuit 515. The switching circuit 525 changes electrical coupling of at least one of the set of pacing electrodes and the set of sensing electrodes.

The control circuit 515 changes the recharge time when a pulse is delivered as part of a threshold test mode and an independent sensing electrode is unavailable. For example, the control circuit 515 initiates a first recharge time duration after delivery of an electrostimulation pulse during the normal pacing mode, and initiates a second recharge time duration after delivery of an electrostimulation pulse that is shorter than the first recharge time duration during the first threshold test mode. In certain examples, the recharge time is reduced to 5 milliseconds (ms) for the second recharge time duration; although the recharge time used may depend on the type of lead coupled to the device 500.

Shortening the recharge time shortens the blanking period used by the device 500. The pace artifact appears sooner and allows for less time to dissipate the residual charge by the device 500. However, the recharge time can be shortened to a point where the difference in dissipation is not that significant and the pacing artifact occurs sooner; allowing the capture signal to be sensed.

If an independent sensing electrode is available for the heart chamber the same recharge time can be used for the threshold test and the normal pacing mode. This is because the independent electrode will not have residual charge at the electrode-tissue interface. Thus, the device 500 may have two threshold modes; one for the case where a sensing electrode independent from the set of pacing electrodes is available for the heart chamber and a second threshold test mode when a sensing electrode independent from the set of pacing electrodes is unavailable.

For instance, the therapy circuit 505 may deliver cardiac electrostimulation energy to the LV during the normal pacing mode using a set of pacing electrodes configured for placement in or near the LV. The control circuit 515 determines whether the electrode configuration includes a sensing electrode for the LV that is independent the set of pacing electrodes. If the electrode configuration includes a sensing electrode for the LV that is independent of the pacing electrodes for the LV, the control circuit 515 initiates the second threshold test mode. If the electrode configuration excludes a sensing electrode for the LV that is independent of the pacing electrodes for the LV, the control circuit initiates the first threshold test mode.

When in the second threshold test mode, the control circuit 515 may recurrently change the electrostimulation energy delivered to the heart chamber, receive a cardiac activity signal sensed using the set of sensing electrodes, initiate the first recharge time duration after delivery of an electrostimulation pulse, and determine an optimum electrostimulation energy for capture of the heart chamber using the sensed cardiac activity signal. The control circuit 515 may determine an electrode configuration electrically coupled to at least one of the cardiac signal sensing circuit 510 and the therapy circuit 505, and initiate the first threshold test mode or a second threshold test mode according to the determined configuration of pacing electrodes. Both the first and second time durations are initiated during a blanking period that includes a time period where the cardiac signal sensing circuit is electrically isolated from the sensing electrodes.

Both the first and second threshold tests determine the optimum pacing energy for evoked response. The control circuit 515, as part of the first and second threshold test modes, delivers electrostimulation energy using a first energy level, and changes the electrostimulation energy level by at least one of: a) increasing the electrostimulation energy from the first energy level until detecting that the electrostimulation energy induces cardiac capture, or b) reducing the electrostimulation energy from the first energy level until detecting that the stimulation energy fails to induce cardiac capture. The control circuit 515 continues the changing of the stimulation energy level until confirming the inducement of stable capture or the failure to induce capture.

The control circuit 515 may then derive an electrostimulation energy value for the normal pacing mode using a determined minimum electrostimulation energy that induces stable capture. In some examples, this derived electrostimulation energy value may be the minimum amplitude that induced capture, or the minimum electrostimulation amplitude or electrostimulation energy plus a safety margin. Once the electrostimulation energy is determined the control circuit 515 may store the derived value in the memory circuit. In certain examples, the control circuit 515 sets the electrostimulation energy of the normal pacing mode using the derived pacing mode. The threshold test has often been described in terms of changing the amplitude of the electrostimulation pulse, but the test may involve changing one or both of the amplitude and the pulse width of the electrostimulation pulse.

The blanking period associated with a pacing pulse may involve both the recharge and clamping of circuits of the pacing interface. As explained previously herein, recharge involves dissipating any residual charge from the pacing by electrically connecting the pacing electrodes together. Clamping attempts to zero-out any DC offset on the electrode-tissue interface. The cardiac signal sensing circuit 510 can include one or more sense amplifier circuits 530 that are biased with a DC reference voltage (e.g., using a reference voltage circuit). As part of the blanking of the sense amplifiers, the control circuit 515 may apply the offset voltage present at the tissue-electrode interface as the DC reference voltage of the sense amplifier at the end of the recharge time.

However, if the electrostimulation pulse includes a negative pace artifact clamping the DC reference voltage to the voltage at the electrode-tissue interface may result in the remaining part of the pace artifact appearing to be a positive voltage deflection associated with cardiac activation. If a threshold test is being executed with an electrode common to the set of pacing electrodes, the pacing artifact could be interpreted as the capture instead of correctly being identified as part of the pacing pulse energy. Thus, when the electrostimulation energy is delivered as part of the normal pacing or the second threshold test (where a sensing electrode independent of the set of pacing electrodes is available) the blanking period includes the first recharge time duration and clamping is performed at the end of the first recharge time duration. When the electrostimulation energy is delivered as part of the first threshold test (in which a sensing electrode independent of the set of pacing electrodes is not available) the blanking period includes the second recharge time and the clamping is not performed (e.g., disabled) at the end of the second recharge time.

In some examples, the cardiac signal sensing circuit 510 includes a filter circuit 535 that performs filtering on the sensed cardiac activity signal. This filtering may produce signal artifacts on the cardiac activity signal that are undesired during a threshold test where an electrode is shared between the pacing vector and the sensing vector. Thus, the control circuit 515 may configure the filter circuit 535 to filter the sensed cardiac activity signal using a first set of filter parameters during the normal pacing mode, and filter the sensed cardiac signal using a second set of filter parameters during the first threshold test mode. The second set of filter parameters results in the filter circuit passing more of the original sensed cardiac activity signal than when using the first set of filtering parameters. For example, the second set of parameters may include less frequency poles and thus pass more signal components of different frequencies than the first set of filtering parameters.

According to some examples, the cardiac signal sensing circuit 510 includes a passive or analog input filter for filtering a sensed cardiac activity signal. In certain examples, the analog filter includes a bandpass filter having a high pass frequency pole (e.g., 0.50 Hertz (Hz)) and a low pass frequency pole (e.g., 100 Hz). The device filtering can also include a digital filter stage, such as implemented by a DSP, which can be configured (such as a bandpass filter) to filter signals resulting from defibrillation or cardioversion shock therapy. In certain examples, the poles of the digital filter are different from the poles of the analog filter (e.g., a high pass frequency of 3.45 Hz and a low pass frequency of 244 Hz).

Filtering can add artifacts a sensed signal. The high pass pole of the bandpass filter tries to eliminate the DC component of a sensed cardiac activity signal. If there is a broad peak in the sensed signal that starts to "look like" DC, the filter will attenuate it. However, it may be desired to preserve as much of the unfiltered signal as possible to determine the evoked response in the signal. Obtaining a more direct and unaltered version of the evoked response signal by turning off the filtering can be useful in the first threshold test mode. In certain examples, the response of the analog filter may not be changeable, but the digital filter can be turned off to obtain a more direct and unaltered version of the evoked response signal.

When the digital filtering is left "on" there is a potential for the Evoked Response signal to have an artificial peak when using a shared electrode. This can happen due to an "overshoot" as the actual signal returns to baseline from a large signal artifact. This overshoot may not be an issue if there is moderate capture signal morphology, but it may be an issue at Loss of Capture (LOC) where there should be no significant capture signal morphology (i.e., the signal just returns to the baseline from the artifact). The overshoot may look like capture or a fusion beats, which is undesirable if the electrostimulation pace pulse is actually related to a LOC.

Different features of an autothreshold test may use different filtering settings. The settings can be one or more of low pass, high pass, and band pass. If there is more than one stage to the digital filtering, these can be used in combination. Additionally, the frequency poles or "corner frequencies" are selectable for each of the stages. Overall, with digital filtering turned on (and in the correct setting), the desired peaks may be more predominant and the less desired peaks may be less dominant, but when there is a sensing electrode in common with a pacing electrode the DSP may create a peak that may not really be there (e.g., the overshoot in the signal). Turning the digital filtering OFF during the first threshold test means that no digital filtering is used during the test, but a more direct and unaltered version of the evoked response signal is obtained.

The devices and methods described herein are often discussed in terms of the LV, but the methods can also be applied to the other heart chambers and to other pacing configurations. If it is desired to perform an auto threshold test for a heart chamber for which a sensing vector is present that is independent of the pacing vector for the heart chamber, sensing for the test can be performed without a significant change to the sensing parameters used for normal pacing. If an independent sensing vector is not present, sensing for the test can still be performed using any combination of the several methods described. Which combination is best may depend on the electrode configuration and the parameters of the sensing circuits.

ADDITIONAL NOTES AND EXAMPLES

Example 1 can include subject matter (such as an apparatus) comprising a therapy circuit configured to provide cardiac electrostimulation energy to a heart chamber of a subject using a set of implantable pacing electrodes, a cardiac signal sensing circuit configured to sense a cardiac activity signal, and a control circuit communicatively coupled to the cardiac signal sensing circuit and the therapy circuit. The control circuit is configured to initiate delivery of electrostimulation energy to the heart chamber according to a normal pacing mode, and initiate a first threshold test mode when receiving an indication to start a threshold test for the heart chamber and a sensing electrode independent from the set of pacing electrodes is unavailable for the heart chamber. When in the first threshold test mode, the control circuit is configured to recurrently change the electrostimulation energy delivered to the heart chamber, receive a cardiac activity signal sensed using a set of sensing electrodes that includes an electrode common to the set of pacing electrodes, and determine an optimum electrostimulation energy for capture of the heart chamber using the sensed cardiac activity signal.

In Example 2, the subject matter of Example 1 can optionally include a switching circuit communicatively coupled to the set of sensing electrodes, the set of pacing electrodes, and the control circuit. The switching circuit is configured to change electrical coupling of at least one of the set of pacing electrodes and the set of sensing electrodes. The control circuit is optionally configured to initiate a first recharge time duration after delivery of an electrostimulation pulse during the normal pacing mode and the set of pacing electrodes are electrically coupled together during a recharge time duration. The control circuit can optionally be configured to initiate a second recharge time duration after delivery of an electrostimulation pulse that is shorter than the first recharge time duration during the first threshold test mode.

In Example 3, the subject matter of Example 2 can optionally include a cardiac signal sensing circuit that includes a sense amplifier circuit that is biased with a DC reference voltage. The control circuit is optionally configured to apply an offset voltage present at a tissue-electrode interface as the DC reference voltage at the end of the first recharge time duration, and to disable applying the offset voltage as the DC reference voltage at the end of the second recharge time duration.

In Example 4, the subject matter of one or any combination of Examples 2 and 3 can optionally include a cardiac signal sensing circuit that includes a filter circuit configured to filter the sensed cardiac activity signal. The filter circuit is optionally configured to filter the sensed cardiac activity signal using a first set of filter parameters during the normal pacing mode, and to filter the sensed cardiac signal using a second set of filter parameters during the first threshold test mode. The second set of filter parameters optionally results in the filter circuit passing more of the original sensed cardiac activity signal than when using the first set of filtering parameters.

In Example 5, the subject matter of one or any combination of Examples 2-4 can optionally include a cardiac signal sensing circuit optionally configured to be electrically isolated from the sensing electrodes during the first and second time durations.

In Example 6, the subject matter of one or any combination of Examples 2-5 can optionally include a control circuit configured to initiate delivery of electrostimulation pulses to a left ventricle (LV) of the subject as part of the normal pacing mode, and change the delivered electrostimulation energy to the LV as part of the first threshold test mode to determine an optimum electrostimulation energy for capture of the LV.

In Example 7 the subject matter of one or any combination of Examples 2-6 can optionally include a control circuit configured to initiate a second threshold test mode when receiving an indication to start a threshold test for the heart chamber and a sensing electrode independent from the set of pacing electrodes is available for the heart chamber. The control circuit can optionally be configured to, while in the second threshold test mode, recurrently change the electrostimulation energy delivered to the heart chamber, receive a cardiac activity signal sensed using a set of sensing electrodes that excludes an electrode common to the set of pacing electrodes, initiate the first recharge time duration after delivery of an electrostimulation pulse, and determine an optimum electrostimulation energy for capture of the heart chamber using the sensed cardiac activity signal.

In Example 8, the subject matter of Example 7 can optionally include an electrode detection circuit communicatively coupled to the control circuit. The control circuit can optionally be configured to determine an electrode configuration electrically coupled to at least one of the cardiac signal sensing circuit and the therapy circuit, and initiate the first threshold test mode or the second threshold test mode according to the determined configuration of pacing electrodes.

In Example 9, the subject matter of Example 8 optionally includes a therapy circuit configured to deliver cardiac electrostimulation energy to the LV during the normal pacing mode using a set of pacing electrodes configured for placement in or near the LV. The control circuit can optionally be configured to determine whether the electrode configuration includes a sensing electrode for the LV that is independent the set of pacing electrodes, initiate the second threshold test mode when the electrode configuration includes a sensing electrode for the LV that is independent of the pacing electrodes for the LV, and initiate the first threshold test mode when the electrode configuration excludes a sensing electrode for the LV that is independent of the pacing electrodes for the LV.

In Example 10, the subject matter of one or any combination of Examples 7-9 can optionally include a control circuit configured to, as part of the first and second threshold test modes, deliver electrostimulation energy using a first energy level, change the electrostimulation energy level by at least one of: a) increasing the electrostimulation energy from the first energy level until detecting that the electrostimulation energy induces cardiac capture, or b) reducing the electrostimulation energy from the first energy level until detecting that the stimulation energy fails to induce cardiac capture, continue the changing of the stimulation energy level until confirming the inducement of stable capture or the failure to induce capture, and derive an electrostimulation energy for the normal pacing mode using a determined minimum electrostimulation energy that induces stable capture.

In Example 11, the subject matter of Example 10 optionally includes a control circuit configured to at least one of: set the electrostimulation energy of the normal pacing mode using the derived pacing mode, and store the derived electrostimulation energy in a memory circuit integral to or coupled to the control circuit.

In Example 12, the subject matter of one or any combination of Examples 10 and 11 optionally include a control circuit configured to change the electrostimulation energy by at least one of changing an amplitude of an electrostimulation pulse and changing a pulse width of the electrostimulation pulse.

In Example 13, the subject matter of one or any combination of Examples 1-12 optionally includes the set of implantable sensing electrodes and the set of pacing electrodes.

Example 14 can include subject matter (such as a method, a means for performing acts, or a machine-readable medium including instructions that, when performed by the machine, cause the machine to perform acts), or can optionally be combined with the subject matter of one or any combination of Examples 1-13 to include such subject matter, comprising delivering cardiac electrostimulation energy to a heart chamber of a subject according to a normal pacing mode using a set of implantable pacing electrodes, and delivering cardiac electrostimulation energy to the subject according to a first threshold test mode when a threshold test for the heart chamber is initiated in the medical device and a sensing electrode independent from the set of pacing electrodes is unavailable for the heart chamber. The first threshold test mode optionally includes: sensing a cardiac activity signal from a subject using a set of sensing electrodes that includes an electrode common to the set of pacing electrodes, and changing the electrostimulation energy and sensing a resulting cardiac activity signal using the set of sensing electrodes to determine an optimum electrostimulation energy for capture of the heart chamber.

In Example 15, the subject matter of Example 14 can optionally include a normal pacing mode that includes initiating a first recharge time duration after delivery of an electrostimulation pulse, and the set of pacing electrodes are electrically coupled together during recharge. The first threshold test mode optionally includes initiating a second recharge time duration after delivery of an electrostimulation pulse that is shorter than the first recharge time duration.

In Example 16, the subject matter of one or any combination of Examples 14 and 15 optionally includes changing a DC reference voltage reference used by the cardiac signal sensing circuit to an offset voltage present at a tissue-electrode interface after delivery of an electrostimulation pulse, and disabling the changing of the DC voltage reference.

In Example 17, the subject matter of one or any combination of Examples 14-16 optionally includes delivering electrostimulation pulses to a left ventricle (LV) of the subject, and wherein the first threshold test mode includes determining an optimum electrostimulation energy for capture of the LV.

In Example 18, the subject matter of one or any combination of Examples 14-17 optionally includes delivering cardiac electrostimulation energy according to a second threshold test mode when a sensing electrode independent of the set of pacing electrodes is available for the heart chamber. The second threshold test mode optionally includes changing the delivered electrostimulation energy and sensing a resulting cardiac activity signal to determine the optimum electrostimulation energy for cardiac capture, and initiating the first recharge time duration after delivery of an electrostimulation pulse.

In Example 19, the subject matter of one or any combination of Examples 14-18 optionally includes filtering the sensed cardiac activity signal using a first set of filter parameters during the normal pacing mode, and filtering the sensed cardiac activity signal using a second set of filter parameters during the first threshold test mode. The second set of filter parameters results in more of the original sensed cardiac activity signal being passed than when filtering using the first set of filtering parameters.

In Example 20, the subject matter of one or any combination of Examples 18 and 19 optionally includes determining, by the medical device, an electrode configuration electrically coupled to the medical device, receiving an indication to initiate a threshold test mode, and initiating the first threshold test mode or the second threshold test mode according to the determined configuration of pacing electrodes.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation of combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus comprising:
   a therapy circuit configured to provide cardiac electrostimulation energy to a heart chamber of a subject using a set of implantable pacing electrodes;
   a cardiac signal sensing circuit configured to sense a cardiac activity signal; and
   a control circuit communicatively coupled to the cardiac signal sensing circuit and the therapy circuit, wherein the control circuit is configured to:
      initiate delivery of electrostimulation energy to the heart chamber according to a normal pacing mode; and
      initiate a first threshold test mode when receiving an indication to start a threshold test for the heart chamber and a sensing electrode independent from the set of pacing electrodes is unavailable for the heart chamber,
      wherein, when in the first threshold test mode, the control circuit is configured to recurrently change the electrostimulation energy delivered to the heart chamber, receive a cardiac activity signal sensed using a set of sensing electrodes that includes an electrode common to the set of pacing electrodes, and determine an optimum electrostimulation energy for capture of the heart chamber using the sensed cardiac activity signal.

2. The apparatus of claim 1, including:
   a switching circuit communicatively coupled to the set of sensing electrodes, the set of pacing electrodes, and the control circuit, wherein the switching circuit is configured to change electrical coupling of at least one of the set of pacing electrodes and the set of sensing electrodes,
   wherein the control circuit is configured to initiate a first recharge time duration after delivery of an electrostimulation pulse during the normal pacing mode, wherein the set of pacing electrodes are electrically coupled together during a recharge time duration, and
   wherein the control circuit is configured to initiate a second recharge time duration after delivery of an electrostimulation pulse that is shorter than the first recharge time duration during the first threshold test mode.

3. The apparatus of claim 2,
   wherein the cardiac signal sensing circuit includes a sense amplifier circuit that is biased with a DC reference voltage,
   wherein the control circuit is configured to apply an offset voltage present at a tissue-electrode interface as the DC reference voltage at the end of the first recharge time duration, and
   wherein the control circuit is configured to disable applying the offset voltage as the DC reference voltage at the end of the second recharge time duration.

4. The apparatus of claim 2,
   wherein the cardiac signal sensing circuit includes a filter circuit configured to filter the sensed cardiac activity signal,
   wherein the filter circuit is configured to:
      filter the sensed cardiac activity signal using a first set of filter parameters during the normal pacing mode; and
      filter the sensed cardiac signal using a second set of filter parameters during the first threshold test mode,
      wherein the second set of filter parameters results in the filter circuit passing more of the original sensed cardiac activity signal than when using the first set of filtering parameters.

5. The apparatus of claim 2,
   wherein the cardiac signal sensing circuit is electrically isolated from the sensing electrodes during the first and second time durations.

6. The apparatus of claim 1, wherein the control circuit is configured to:
   initiate delivery of electrostimulation pulses to a left ventricle (LV) of the subject as part of the normal pacing mode, and
   change the delivered electrostimulation energy to the LV as part of the first threshold test mode to determine an optimum electrostimulation energy for capture of the LV.

7. The apparatus of claim 2,
   wherein the control circuit is configured to initiate a second threshold test mode when receiving an indication to start a threshold test for the heart chamber and a sensing electrode independent from the set of pacing electrodes is available for the heart chamber;
   wherein, while in the second threshold test mode, the control circuit is configured to recurrently change the electrostimulation energy delivered to the heart chamber, receive a cardiac activity signal sensed using a set of sensing electrodes that excludes an electrode common to the set of pacing electrodes, initiate the first recharge time duration after delivery of an electrostimulation pulse, and determine an optimum electrostimulation energy for capture of the heart chamber using the sensed cardiac activity signal.

8. The apparatus of claim 7, including:
   an electrode detection circuit communicatively coupled to the control circuit, and
   wherein the control circuit is configured to:
      determine an electrode configuration electrically coupled to at least one of the cardiac signal sensing circuit and the therapy circuit; and
      initiate the first threshold test mode or the second threshold test mode according to the determined configuration of pacing electrodes.

9. The apparatus of claim 8,
   wherein the therapy circuit is configured to deliver cardiac electrostimulation energy to the LV during the normal pacing mode using a set of pacing electrodes configured for placement in or near the LV,
   wherein the control circuit is configured to:
      determine whether the electrode configuration includes a sensing electrode for the LV that is independent the set of pacing electrodes;
      initiate the second threshold test mode when the electrode configuration includes a sensing electrode for the LV that is independent of the pacing electrodes for the LV; and
      initiate the first threshold test mode when the electrode configuration excludes a sensing electrode for the LV that is independent of the pacing electrodes for the LV.

10. The apparatus of claim 7, wherein the control circuit, as part of the first and second threshold test modes, is configured to:
    deliver electrostimulation energy using a first energy level;
    change the electrostimulation energy level by at least one of: a) increasing the electrostimulation energy from the first energy level until detecting that the electrostimulation energy induces cardiac capture, or b) reducing the electrostimulation energy from the first energy level until detecting that the stimulation energy fails to induce cardiac capture;

continue the changing of the stimulation energy level until confirming the inducement of stable capture or the failure to induce capture; and derive an electrostimulation energy for the normal pacing mode using a determined minimum electrostimulation energy that induces stable capture.

11. The apparatus of claim 10, wherein the control circuit is configured to at least one of:

set the electrostimulation energy of the normal pacing mode using the derived pacing mode; and store the derived electrostimulation energy in a memory circuit integral to or coupled to the control circuit.

12. The apparatus of claim 10, wherein the control circuit is configured to change the electrostimulation energy by at least one of changing an amplitude of an electrostimulation pulse and changing a pulse width of the electrostimulation pulse.

13. The apparatus of claim 1, wherein the apparatus includes the set of implantable sensing electrodes and the set of pacing electrodes.

14. A method of operating a medical device comprising:

delivering cardiac electrostimulation energy to a heart chamber of a subject according to a normal pacing mode using a set of implantable pacing electrodes; and delivering cardiac electrostimulation energy to the subject according to a first threshold test mode when a threshold test for the heart chamber is initiated in the medical device and a sensing electrode independent from the set of pacing electrodes is unavailable for the heart chamber, wherein the first threshold test mode includes:

sensing a cardiac activity signal from a subject using a set of sensing electrodes that includes an electrode common to the set of pacing electrodes; and changing the electrostimulation energy and sensing a resulting cardiac activity signal using the set of sensing electrodes to determine an optimum electrostimulation energy for capture of the heart chamber.

15. The method of claim 14, wherein the normal pacing mode includes initiating a first recharge time duration after delivery of an electrostimulation pulse, wherein the set of pacing electrodes are electrically coupled together during recharge, and wherein the first threshold test mode includes initiating a second recharge time duration after delivery of an electrostimulation pulse that is shorter than the first recharge time duration.

16. The method of claim 15, wherein delivering cardiac electrostimulation energy to the subject according to a normal pacing mode includes changing a DC reference voltage reference used by the cardiac signal sensing circuit to an offset voltage present at a tissue-electrode interface after delivery of an electrostimulation pulse, and wherein delivering cardiac electrostimulation energy to the subject according to the first threshold test mode includes disabling the changing of the DC voltage reference.

17. The method of claim 14, wherein the normal pacing mode includes delivering electrostimulation pulses to a left ventricle (LV) of the subject, and wherein the first threshold test mode includes determining an optimum electrostimulation energy for capture of the LV.

18. The method of claim 14, including:

delivering cardiac electrostimulation energy according to a second threshold test mode when a sensing electrode independent of the set of pacing electrodes is available for the heart chamber, wherein the second threshold test mode includes:

changing the delivered electrostimulation energy and sensing a resulting cardiac activity signal to determine the optimum electrostimulation energy for cardiac capture; and initiating a first recharge time duration after delivery of an electrostimulation pulse.

19. The method of claim 18, including:

filtering the sensed cardiac activity signal using a first set of filter parameters during the normal pacing mode; and filtering the sensed cardiac activity signal using a second set of filter parameters during the first threshold test mode, wherein the second set of filter parameters results in more of the original sensed cardiac activity signal being passed than when filtering using the first set of filtering parameters.

20. The method of claim 18, including:

determining, by the medical device, an electrode configuration electrically coupled to the medical device;

receiving an indication to initiate a threshold test mode; and initiating the first threshold test mode or the second threshold test mode according to the determined configuration of pacing electrodes.

* * * * *